United States Patent [19]

Olivieri et al.

[11] 4,312,948

[45] Jan. 26, 1982

[54] ENZYMIC MICROBIOLOGICAL PROCESS FOR PRODUCING OPTICALLY ACTIVE AMINOACIDS STARTING FROM HYDANTOINS AND/OR RACEMIC CARBAMOYL DERIVATIVES

[75] Inventors: Roberto Olivieri, Mentana; Aurelio Viglia, Monterotondo; Ludwig Degen, Rome; Leonello Angelini, Monterotondo; Eugenio Fascetti, Rome, all of Italy

[73] Assignee: Snamprogetti S.p.A., Milan, Italy

[21] Appl. No.: 38,232

[22] Filed: May 11, 1979

[30] Foreign Application Priority Data

May 23, 1978 [IT] Italy ............................... 23679 A/78

[51] Int. Cl.³ .......................... C12N 1/20; C07B 19/02
[52] U.S. Cl. .................................. 435/253; 435/106; 435/280; 435/822
[58] Field of Search ..................... 435/280, 106–108, 435/253

[56] References Cited

U.S. PATENT DOCUMENTS

| | | | |
|---|---|---|---|
| 4,065,353 | 12/1977 | Cecere et al. | 435/280X |
| 4,094,741 | 6/1978 | Yamada et al. | 435/280 |
| 4,111,749 | 9/1978 | Degen et al. | 435/280 |
| 4,204,044 | 5/1980 | Suhara et al. | 435/280 |
| 4,211,840 | 7/1980 | Nakamori et al. | 435/107 |

*Primary Examiner*—Lionel M. Shapiro
*Attorney, Agent, or Firm*—Morgan, Finnegan, Pine, Foley & Lee

[57] ABSTRACT

A method is disclosed for producing D-aminoacids from racemic mixtures of N-carbamoyl derivatives of such acids or from the corresponding hydantoins wherein the racemic compounds are subjected to the enzymic and microbiological action of an enzymic complex prepared from microorganisms of the Agrobacterium genus, more particularly the NRRL B 11291 strain.

6 Claims, No Drawings

ENZYMIC MICROBIOLOGICAL PROCESS FOR PRODUCING OPTICALLY ACTIVE AMINOACIDS STARTING FROM HYDANTOINS AND/OR RACEMIC CARBAMOYL DERIVATIVES

This invention relates to a process for producing D-aminoacids starting from racemic mixtures of their N-carbamoyl derivatives or from the corresponding hydantoins by employing stereospecific enzymic complexes obtained from micro-organisms of the Agrobacterium genus.

A few D-aminoacids, especially phenylglycine and p-hydroxy phenylglycine are important intermediates for the preparation of compounds which are widely used in the pharmaceutical industry.

The chemical methods adopted heretofore for the separation of the optical antipodes, and which are based on the use of camphosulfonic acid are very expensive and give low yields.

Another method consists in hydrolyzing the D-acylamino acid with the D-acylase enzyme.

These enzymic preparations, however, have always L-acylase as an impurity, that which leads to the obtention of a product having a poor optical purity.

A method for the enzymic resolution of D,L-aminoacids or of derivatives thereof has already been suggested by the same Assignee hereof in the Italian Pat. No. 987.278, U.S. patent application No. 885,194 U.S. Pat. No. 4,248,967, U.S. Pat. No. 4,111,749, respectively filed on Feb. 20, 1975, Mar. 10, 1978, Sept. 7, 1976.

The method mentioned above substantially consists in subjecting to an enzymic hydrolysis by hydropyrimidine hydrolase (E.C.3.5.2.2.) as extracted from organs or from microorganisms, the racemic form of compounds having the following general formula:

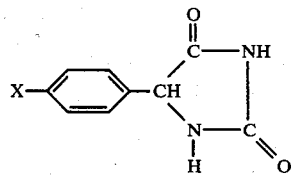

X = —H, —OH, —OCH$_3$

The hydrolysis takes place according to the following pattern:

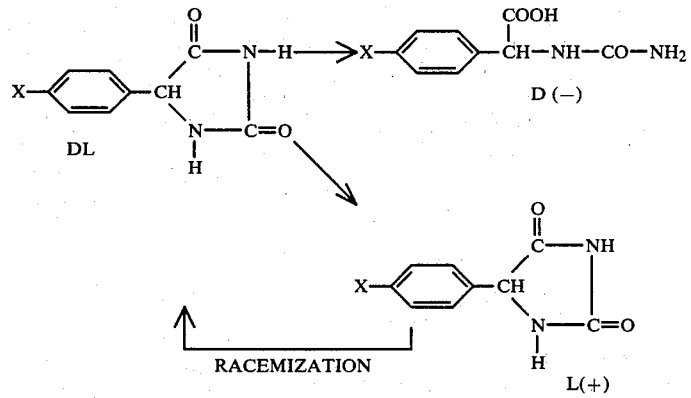

Subsequently, the N-carbamoyl derivative is degraded to D-aminoacid by oxidation with a nitrite according to the method disclosed by the same Assignee in the U.S. patent application No. 674,763 filed on Apr. 8, 1976.

The method according to the present invention is characterized in that the D-aminoacids are produced from the corresponding hydantoins by exploiting hydrolytic reactions which are catalyzed exclusively by enzymic complexes, according to the following pattern:

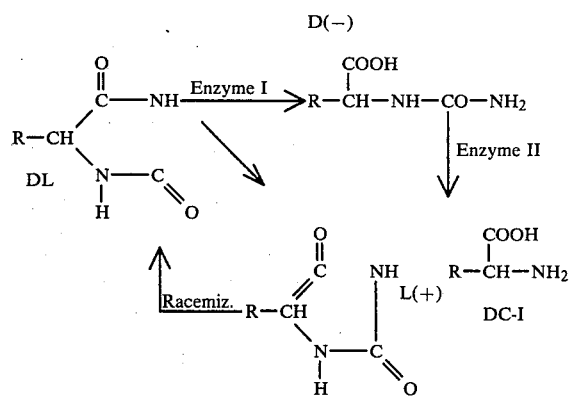

wherein R can be an aliphatic or aromatic radical, either substituted or unsubstituted.

The method according to the present invention, moreover, is characterized in that D-aminoacids can be obtained also starting from racemic compounds having the following general formula:

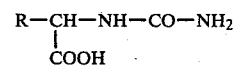

in which R is a member selected from the group consisting of the substituted and the unsubstituted aliphatic and aromatic radicals, the Enzyme II (carbamoylase) being stereoselective towards the D-forms.

The enzymic hydrolysis of the present invention takes place according to the pattern reported hereunder and has, as its result, the production of a single stereoisomeric form of an aminoacid and of a derivative thereof starting from a racemic compound:

$$\underset{DL}{\underset{|}{\overset{H}{\underset{COOH}{|}}}} R-\overset{H}{\underset{|}{C}}-NHCONH_2 \xrightarrow{carbamoylase} \underset{D(-)}{\underset{|}{\overset{H}{\underset{COOH}{|}}}} R-\overset{H}{\underset{|}{C}}-NH_2$$

$$\underset{L(+)}{R-\overset{H}{\underset{|}{\underset{COOH}{|}}}-NHCONH_2}$$

The enzymic preparations described in the present invention are, contrarily to those which contain D-acylase, completely devoid of any activity on the L-enantiomeride. This circumstance permits that D-aminoacids having an absolute optical purity may be obtained.

The enzymic complexes according to the present invention are produced by microorganisms of the Agrobacterium genus, isolated from agricultural land and marked with the numerals 1302, 1303 and 1304.

They have the following morphological and biochemical properties:

Microscopical morphology

Discrete rods, sometimes paired, gram-negative, $0.8 \times 1.5$ to 2.0 microns, capsula and spores absent; mobile with 4 to 6 peritrichial flagella.

Macroscopic morphology

Colonies on agar nutrient (Difco): lifted, uninterrupted edge, cream-colored, transparent, 0.5 to 1 mm diameter, the smooth surface. Luxuriant growth on calcium glycerophosphate-mannitol nitrate-agar, with browning and halo formation.

Biochemical characteristics

Growth between 4° C. and 39° C. on all simple laboratory media, also without growth factors and aminoacids, using $NH_4^+$, $NO_3^-$ or aminoacids as the only nitrogen sources.

Oxidase: positive (N. Kovacs, 1956, Nature, London, 178, 703).

Catalase: positive (M. Levine, D. Q. Anderson, 1932, J. Bact. 23, 337–347).

Nitrites produced from nitrates (C. E. Zobell, 1932, J. Bact. 24, 273).

Twenn 80 not hydrolyzed (C. Sierra, 1957, Antonie van Leeuwenhoek, 23, 15–22).

Casein, gelatin, cellulose, starch, agar: not hydrolyzed.

(V. B. D. Skermann, A Guide to the Identification of the Genera of Bacteria, 2nd Edition, The Williams & Wilkins Book Co., Baltimore, 1967).

3-ketoglycosides produced (M. J. Bernaerts, J. De Ley, 1963, Nature 197, 406).

Aniline Blue-mannitol-agar: growth with absorption of the dye (A. A. Hendrickson, J. L. Baldwin, A. J. Riker, 1934, J. Bact. 28, 597–618)

Litmus milk: grey-brown.

Utilization of carbohydrates: oxidative (R. Hugh, E. Leifson, 1953, J. Bact. 66, 24–26).

The following compounds are used as the only carbon sources in the medium for the purpose described by R. Y. Stanier, (R. Y. Stanier et Al., 1966, J. Gen. Microbiol 43, 159-271: D(+)glucose, L(+)arabinose, D(+)xylose, D(+)threose, D(+)threalose, D(−)rinose, L(+)rhamnose, lactose, cellobiose, maltose, citrate, acetate, lactate, propionate, L-aspartic, L-asparagine, L-histidine, L-alanine, L-arginine.

Comparing these properties with the descriptions in Bergey's Manual of Determinative Bacteriology, VIII Edition, the microorganisms belonging to the invention are of the Rhizobiaceae family, Agrobacterium genus.

The strain marked No. 1302 has been deposited on the Apr. 6, 1978 with the Northern Regional Research Center of Peoria, Ill., U.S.A., where it has been attributed the symbol NRRL B 11291.

According to the present invention, the microorganisms of the genus Agrobacterium are cultured under aerobic conditions in a culturing medium which contains sources of nitrogen, carbon, phosphorus, and mineral salts at a temperature comprised between 20° C. and 40° C., preferably between 25° C. and 35° C. for a period of from 10 hours to 48 hours, preferably between 20 hrs and 30 hrs, at a pH of 6.0–8.0, preferably 7 to 7.5. Glucose, lactate, acetate, corn steep liquor and lactose can be used as carbon sources.

Meat hydrolysates, hydrolysates of casein and soybean, ammonium salts and urea, hydantoins and N-carbamoyl derivatives of aminoacids are nitrogen sources.

An appropriate culturing medium has, for example, the following composition:

| | |
|---|---|
| Meat peptone | 5 g |
| Meat extract | 5 g |
| Glucose | 5 g |
| Distilled water | 1,000 mls |
| pH | 7.0-7.2 |

D(−)aminoacids are directly produced in the fermentation media which contain DL-hydantoins or DL-N-carbamoyl derivatives of aminoacids, both as single sources of nitrogen and integrated with the usual nitrogen sources.

D(−)aminoacids can also be produced by directly using the microbial slurry as resting cells or using extracts of it.

The extraction, from the bacterial slurry, of the enzyme complexes of the present invention takes place with the usual methods adopted in enzymology.

For this purpose, the cells are disintegrated with appropriate apparatus, e.g. French Pressure Cell Press, Manton Gauling Homogenizer, rotary disintegrators and also with ultrasonic vibrators.

The hydrolysis of the hydantoins or of the N-carbamoyl derivatives of the aminoacids can be carried out by adding to the reaction mixture the enzyme in the following forms: fresh cells, freeze-dried cells, toluenized cells, acetonic powder or raw or purified extracts.

An additional technical and economical improvement can be achieved by immobilizing the enzymes by combination with macromolecular compounds by formation of chemical bonds with the matrix or bonds of ionic type or by physical immobilization.

The examples given hereinafter disclose other operative details of the present invention but are not limiting.

EXAMPLE 1

A culturing broth has been prepared with the following composition:

| | |
|---|---|
| Meat peptone | 5 g |
| Meat extract | 3 g |
| Glucose | 5 g |
| Distilled water | 1,000 mls |

The pH was adjusted to 7.2 with soda and the culturing medium was distributed, in 100-ml portions, in 500-ml flasks.

After sterilization for 30 mins at 110° C. the flasks were inoculated with a culture of the strain No. 1302 from slants containing the same medium with the 2% of agar (DIFCO) and incubated for 24 hrs. at 30° C. with orbital stirring (220 RPM).

From this pre-culture (D.O. at 550 nm: 0.250 dil×1:10) there were inoculated 1 ml in five 500-ml flasks containing 100 mls of the same medium and the culture was incubated at 30° C. with orbital stirring (220 RPM) for 24 hours (D.O. at 550 nm-0.250; dil. 1:10).

The cells were subsequently collected, washed in a physiological solution and finally slurried in 100 mls of pyrophosphate buffer (0.1 m; pH 7.7) containing 10 g of D,L-5-phenylhydantoins at the temperature of 40° C. under a UPP nitrogen blanket.

After 200 hours of incubation under these conditions, the complete hydrolysis to aminoacid (D-phenylglycine) was achieved as evidenced both by the polarimetric analysis of the reaction mixture and by the thin-layer chromatography according to the procedure disclosed by Suzuki in J. of Chromatography, 80 (1973), 199-204.

The aminoacid was isolated from the reaction mixture upon precipitation of the proteins with trichloroacetic acid and their removal by centrifugation, the pH being brought to the isoelectric point (5.8).

The precipitate was washed with water and dried in vacuum. The identity of the D(−)phenylglycine aminoacid was confirmed by the IR and NMR spectra.

The specific optical power was $[\alpha]_D^{25} = -154$ degrees. (c=1% in HCl 1 N) against a value of −157.8 reported by the literature for the pure aminoacid.

EXAMPLE 2

Cells prepared as in Example 1 coming from 100 mls of broth culture were slurried in 10 mls of pyrophosphate buffer (0.1 M, pH 7.7) and subjected to sonication at 5° C. for 10 mins. The sonicate was added to 500 mls of a solution of D,L-N-carbamoylphenylglycine 20 mM in pyrophosphate buffer (0.1 M pH 7.7) and incubated at 65° C.

The kinetics of the reaction was monitored by reading the ammonium set free in the hydrolysis of the N-carbamoyl with the phenol-hypochloride method.

After a 40-hour incubation, the $NH_4^+$ ion had attained the concentration of 10 millimols per liter and no further increases were recorded with the lapse of time.

The reaction mixture was concentrated at 50° C. under vacuum up to 100 mls.

When the pH was adjusted to 5.8 with concentrated HCl, a precipitate was collected on a filter.

The precipitate thus obtained was dissolved in 1 N HCl and reprecipitated with NaOH at a pH of 5.8.

After drying, the specific optical rotatory power was determined and was −153°. The IR spectrum confirmed the identity of the aminoacid.

From the filtrate, cautiously adjusted to a pH 2.5 with 3 N HCl on an ice bath a precipitate was obtained which was evaporated to dryness and extracted with absolute boiling ethanol. Upon cooling, the alcoholic solution gave a crystalline precipitate which was subjected upon drying to thin-layer chromatography and IR spectrum test.

These analyses confirmed that chemically pure N-carbamoylphenyl glycine was present.

The specific optical rotatory power was $[\alpha]_D^{25} = 134°$ (c=1% in 1 N NaOH) against the value of +137° reported by the literature for the L-enantiomeride.

EXAMPLE 3

From a preculture prepared as in Example 1 there were inoculated five 500-ml flasks each containing 100 mls of a medium exclusively composed by a 5% solution of corn steep liquor brought to pH 7.8 with NaOH and sterilized at 121° C. for 30 mins.

The culture was incubated for 24 hrs. at 30° C. with orbital stirring (220 RPM). The cells collected by centrifugation were washed with pyrophosphate buffer (0.1 M pH 7.7) and then slurried in 100 mls of the same buffer containing 10 grams of 5-parahydroxy-D,L-phenylhydantoins and incubated at 40° C. under a UPP nitrogen blanket. After 160 hrs. of incubation under these conditions the complete hydrolysis to aminoacid (parahydroxyphenyl glycine D(−)) was achieved, as confirmed both by the polarimetric test of the reaction mixture and by the thin-layer chromatography test made according to Suzuki (J. of Chromatography, 80 (1973) 199-204.

The aminoacid was isolated from the reaction mixture upon precipitation of the proteins with trichloroacetic acid and their removal by centrifugation, the pH being brought to the isoelectric point (5.2). The precipitate was washed with water and vacuum dried. The identity of the aminoacid was confirmed on the basis of the IR and NMR spectra. The specific optical rotatory power was $[\alpha]_D^{25} = -156.5°$ (c=1% in 1 N HCl), against a value of −161.2° reported by the literature for the pure aminoacid.

EXAMPLE 4

Cells are used which are of the strain Agrobacterium sp. coming from 100 mls of broth culture based on corn steep liquor and prepared as in Example 1.

The washed cells were slurried in 10 mls of pyrophosphate buffer (0.1 M pH 7.7) and subjected to toluenization for 15 mins with stirring at room temperature.

The toluenized slurry was added to 500 mls of a solution of N-carbamoyl-D,L-parahydroxyphenylglycine 20 mM in pyrophosphate buffer (0.1 M pH 7.7) and incubated at 65° C. under a UPP nitrogen blanket.

The kinetics of the reaction were monitored by reading out the ammonium set free in the hydrolysis of N-carbamoyl derivative according to the method of phenol-hypochlorite as mentioned in Example 1.

After 18 hours of incubation, the $NH_4^+$ ions had attained the concentration of 10 millimols per liter and no further increases in time were recorded.

At this stage, the reaction mixture was concentrated in vacuum at 50° C. to a final volume of 100 mls. When the pH was adjusted to 5.2 with concentrated HCl, a precipitate was obtained and collected on a filter.

By following exactly the same procedures as described in Example 2 the D-aminoacid and the N-carbamoyl-L were isolated and identified and the specific optical rotatory powers were, respectively, −157.2° and +171° against the values of −161.2° and +175.4 as reported by the literature for the pure products.

EXAMPLE 5

Cells of Agrobacterium sp. strain were prepared as described in Example 1. A few grams of moist cellule slurry was slurried in pyrophosphate buffer (0.1 M pH 7.7) and subjected to acetonic treatment in the cold.

After removing acetone by filtration, the acetonic preparation thus obtained was dried to constant weight in vacuum at 35° C. The dried material was homogenized in a mortar and powder thus obtained was used for the enzymic activity tests.

The caetonic powder was assayed on the following substrates: N-carbamoyl-D-(−)-alanine, N-carbamoyl-D(−) valine, N-carbamoyl-D-(−)glutamic acid, N-carbamoyl-D(−)-parahydroxyphenylglycine, N-carbamoyl-D(−)-paramethoxyphenylglycine, N-carbamoyl-D-(−)-phenylglycine, N-carbamoyl-L(+)-phenylglycine, N-carbamoyl-D(−)-phenylalanine, N-carbamoyl-L(+)-glutamic acid and N-carbamoyl-D(−) (2-thienyl)-glycine.

Thus, 20 mM solution were prepared of each carbamoyl derivative in pyrophosphate buffer 0.1 M pH 7.7, and, to 10 mls of each solution there was added an adequate quantity of acetonic powder, equal for each substrate.

The incubation was carried out under a UPP nitrogen blanket with stirring at a temperature of 40° C. After 1-hour incubation, the quantity of the produced aminoacid was measured by determining in the reaction mixtures the concentration of the $NH_4^+$ ion which has been reached, with the phenol-hypochlorite method indicated in Example 2.

It has been found that the highest activity of the carbamoylytic enzyme is unfolded against N-carbamoyl-D(−)-parahydroxy phenylglycine.

TABLE 1 reports the results of the tests, assuming as 100 the hydrolytic activity displayed against N-carbamoyl-D(−)-parahydroxyphenylglycine.

TABLE 1

| SUBSTRATE | % ACTIVITY |
| --- | --- |
| N-carbamoyl-D-(−)-alanine | 57.5 |
| N-carbamoyl-D(−)-valine | 34.25 |
| N-carbamoyl-D(−)glutamic acid | 21.7 |
| N-carbamoyl-L(+)glutamic acid | 0 |
| N-carbamoyl-D(−)-parahydroxy-phenylglycine | 100.0 |
| N-carbamoyl-D(−)-paramethoxy-phenylglycine | 40.0 |
| N-carbamoyl-D(−)-phenylglycine | 81.25 |
| N-carbamoyl-L(+)-phenylglycine | 0 |
| N-carbamoyl-D(−)-(2-thienyl) glycine | 40.7 |
| N-carbamoyl-D(−)-phenylalanine | 50.0 |

EXAMPLE 6

A culturing broth was prepared with the following composition:

| | |
| --- | --- |
| $MgSO_4.7H_2O$ | 0.2 g |
| $Na_2HPO_4.12H_2O$ | 6 g |
| $KH_2PO_4$ | 3 g |
| $NH_4Cl$ | 2 g |
| NaCl | 0.5 g |
| Glycerol | 5 g |
| 5-phenyl-D,L-hydantoins | 2 g |
| Yeast extract | 0.1 g |
| Distilled water | 1,000 mls |

The medium, distributed in 100-ml portions in 500-ml flasks, was sterilized at 116° C. for 30 minutes. Hydantoin was sterilized by filtration.

From a pre-culture prepared as in Example 1 there were inoculated 5 mls per flask and the culture was incubated at 30° C. with 220 RPM orbital stirring for 36 hours. Subsequently, the cells were removed by centrifugation and the aminoacid was collected from the supernatant upon concentration and adjustment to the isoelectric point of said supernatant. From 10 liters of a thus treated culture broth there were recovered 11.2 grams of D(−)-phenylglycine the specific optical rotatory power was $[\alpha]_D^{25} = -156°$ (c=1% in 1 N HCl) against a value of −157.8° as reported by the literature for the pure aminoacid.

EXAMPLE 7

A culturing broth was prepared with the following composition:

| | |
| --- | --- |
| $MgSO_4.7H_2O$ | 0.2 g |
| $Na_2HPO_4.12H_2O$ | 6 g |
| $KH_2PO_4$ | 3 g |
| 5-methyl-hydantoin | 2 g |
| NaCl | 0.5 g |
| Glucose | 1 g |
| Yeast extract | 0.1 g |
| Distilled water | 1,000 mls |
| pH | 7.1 |

The culturing medium, distributed in 100-ml portions in 500-ml flasks, was sterilized at 116° C. for 20 mins. Methylhydantoin was sterilized separately.

From a preculture prepared as in Example 1, were inoculated 5 mls per flask and the culture was incubated at 30° C. with orbital stirring (220 RPM) for 24 hours.

The cellular slurry which has been collected by centrifugation from 1,000 mls of broth was washed in phosphate buffer (pH 7.5) and reslurried in 100 mls of the same buffer containing 4 g of DL-5-(2-thienyl)-hydantoin.

The reaction mixture was incubated at 40° C. under a UPP nitrogen blanket. After 30 hours of reaction there was completed the hydrolysis to the aminoacid (D(−) (2-thienyl)glycine). The aminoacid was isolated by concentrating the reaction mixture to a final volume of 20 mls and by adjusting the pH to 5.6. The precipitate thus obtained was vacuum dried. The identity of the aminoacid was confirmed by the IR and NMR spectra.

The specific optical rotatory power was $[\alpha]_D^{25} = -72.6°$ (c=1% in $H_2O$) against a value of −73.7° as reported in the literature for the pure aminoacid.

We claim:

1. Method for the production of D-aminoacid starting from racemic mixtures of their N-carbamoyl derivatives or from the corresponding hydantoins, characterized in that the reaction is carried out in the pressure of enzymic complexes obtained from a microorganism of the Agrobacterium genus identified by the symbol NRRL B 11291.

2. Method for the preparation of hydantoins according to claim 1 wherein the hydantoin is D,L-5-phenyl-hydantoin.

3. Method for the preparation of D-aminoacids according to claim 1 wherein the aminoacid is D,L-N-carbamoylphenylglycine.

4. Method for the preparation of hydantoins according to claim 1 wherein the hydantoin is 5-parahydroxy-D,L-phenyl-hydantoin.

5. Method for the preparation of D-aminoacids according to claim 1 wherein the aminoacid is N-carbamoyl-D,L-parahydroxy-phenylglycine.

6. A biologically pure culture of Agrobacterium NRRL B 11291, said culture being capable of producing D-aminoacids from racemic mixtures of their N-carbamoyl derivatives or the corresponding hydantoins.

* * * * *